United States Patent [19]
Blum et al.

[11] Patent Number: 6,153,576
[45] Date of Patent: Nov. 28, 2000

[54] TRANSITION-METAL COMPLEXES USED AS ACTIVATORS FOR PEROXY COMPOUNDS

[75] Inventors: Helmut Blum; Bernd Mayer; Ulrich Pegelow, all of Duesseldorf; Horst-Dieter Speckmann, Langenfeld; Bernt Krebs, Muenster; Mark Duda, Iserlohn; Cetin Nazikkol, Duisburg; Joerg Reim, Duelmen, all of Germany

[73] Assignee: Henkel Kommanditgesellschaft Auf Aktien, Duesseldorf, Germany

[21] Appl. No.: 09/125,332

[22] PCT Filed: Feb. 7, 1997

[86] PCT No.: PCT/EP97/00550

§ 371 Date: Sep. 16, 1998

§ 102(e) Date: Sep. 16, 1998

[87] PCT Pub. No.: WO97/30144

PCT Pub. Date: Aug. 21, 1997

[30] Foreign Application Priority Data

Feb. 16, 1996 [DE] Germany ............ 196 05 688

[51] Int. Cl.⁷ .................... C11D 3/28; C11D 3/395
[52] U.S. Cl. ............. 510/311; 510/312; 510/376
[58] Field of Search ............... 510/311, 312, 510/376, 303

[56] References Cited

U.S. PATENT DOCUMENTS

| | | | |
|---|---|---|---|
| 4,585,642 | 4/1986 | Rieck | 423/333 |
| 4,590,237 | 5/1986 | Wuhrmann et al. | 524/480 |
| 4,664,839 | 5/1987 | Rieck | 252/175 |
| 4,820,439 | 4/1989 | Rieck | 252/135 |
| 4,832,866 | 5/1989 | Schulz et al. | 252/321 |
| 4,865,774 | 9/1989 | Fabry et al. | 252/554 |
| 5,002,695 | 3/1991 | Schulz et al. | 252/321 |
| 5,183,651 | 2/1993 | Schimmel et al. | 423/334 |
| 5,229,095 | 7/1993 | Schimmel et al. | 423/334 |
| 5,236,682 | 8/1993 | Schimmel et al. | 423/334 |
| 5,268,156 | 12/1993 | Schimmel et al. | 423/334 |
| 5,308,596 | 5/1994 | Kotzian et al. | 423/333 |
| 5,318,733 | 6/1994 | Carduck et al. | 264/15 |
| 5,356,607 | 10/1994 | Just | 423/334 |
| 5,358,655 | 10/1994 | Kruse et al. | 252/95 |
| 5,382,377 | 1/1995 | Raehse et al. | 252/174 |
| 5,417,951 | 5/1995 | Just | 423/334 |
| 5,494,488 | 2/1996 | Arnoldi et al. | 8/137 |
| 5,541,316 | 7/1996 | Engelskirchen et al. | 510/471 |
| 5,580,941 | 12/1996 | Krause et al. | 527/300 |
| 5,733,341 | 3/1998 | Eckhardt et al. | 8/111 |

FOREIGN PATENT DOCUMENTS

| | | |
|---|---|---|
| 94 58592 | 8/1994 | Australia . |
| 1 036 455 | 8/1978 | Canada . |
| 0 028 865 | 5/1981 | European Pat. Off. . |
| 0 080 223 | 6/1983 | European Pat. Off. . |
| 0 080 748 | 6/1983 | European Pat. Off. . |
| 0 150 386 | 8/1985 | European Pat. Off. . |
| 0 164 514 | 12/1985 | European Pat. Off. . |
| 0 164 552 | 12/1985 | European Pat. Off. . |
| 0 262 588 | 4/1988 | European Pat. Off. . |
| 0 294 753 | 12/1988 | European Pat. Off. . |

(List continued on next page.)

OTHER PUBLICATIONS

Z. Zhang, S. Ma, X. Yang, G. Ma, Huaxue yanjiu Yu Yingyong vol. 7, 1995, pp. 137–141 (abstract).
Chemical Abstracts 116:186561.
Chemical Abstracts 117:236692.
Chemical Abstracts 118:8928.
Chemical Abstracts 122:317488.
Chemical Abstracts 125:68828.
Derwent WPAT Abstract No. 95–009705/02.
Derwent WPAT Abstract No. 96–011551/02.
Derwent WPAT Abstract No. 96–287166/29.
Derwent WPAT Abstract No. 93–259656/33.
Derwent WPAT Abstract No. 94–035002/04.
Derwent WPAT Abstract No. 94–235530/29.
Derwent WPAT Abstract No. 94–280420/35.
Derwent WPAT Abstract No. 96–000404/01.
Derwent WPAT Abstract No. 74–7575V/44.
Derwent WPAT Abstract No. 85–270605/44.
Derwent WPAT Abstract No. 91–126877/18.
Derwent WPAT Abstract No. 91–172613/24.
Derwent WPAT Abstract No. 92–335303/41.
Derwent WPAT Abstract No. 92–360500/44.
Derwent WPAT Abstract No. 93–206465/26.

(List continued on next page.)

*Primary Examiner*—John R. Hardee
*Attorney, Agent, or Firm*—Wayne C. Jaeschke; Glenn E.J. Murphy

[57] ABSTRACT

Described are complexes of the transition metals manganese, iron, cobalt, ruthenium, molybdenum, titanium, vanadium and/or copper containing one or more ligands of general formula (I) ou (II) in which R is a direct bond or an optionally amin-group-substituted alkylene group with 1 to 4 C-atoms, A is a condensed or non-condensed ring system containing at least one nitrogen atom, B is hydrogen, an OH-group or the same as A, and X is a phenyl ring optionally substituted with and/or $C_{1-4}$ alkyl or an optionally hydroxy-substituted $C_{1-4}$ alkylene group. The complexes are suitable for use as activators or peroxy compounds in oxidative washing, cleaning and disinfectant solutions, washing and cleaning agents preferably containing 0.0025 to 0.25% by wt. of such activator complexes.

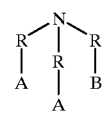

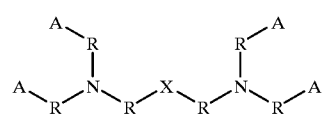

13 Claims, No Drawings

FOREIGN PATENT DOCUMENTS

| | | |
|---|---|---|
| 0 301 414 | 2/1989 | European Pat. Off. . |
| 0 309 931 | 4/1989 | European Pat. Off. . |
| 0 376 705 | 7/1990 | European Pat. Off. . |
| 0 378 261 | 7/1990 | European Pat. Off. . |
| 0 378 262 | 7/1990 | European Pat. Off. . |
| 0 392 592 | 10/1990 | European Pat. Off. . |
| 0 425 427 | 5/1991 | European Pat. Off. . |
| 0 425 428 | 5/1991 | European Pat. Off. . |
| 0 436 835 | 7/1991 | European Pat. Off. . |
| 0 443 651 | 8/1991 | European Pat. Off. . |
| 0 451 924 | 10/1991 | European Pat. Off. . |
| 0 458 397 | 11/1991 | European Pat. Off. . |
| 0 458 398 | 11/1991 | European Pat. Off. . |
| 0 486 592 | 5/1992 | European Pat. Off. . |
| 0 502 325 | 9/1992 | European Pat. Off. . |
| 0 511 456 | 11/1992 | European Pat. Off. . |
| 0 544 490 | 6/1993 | European Pat. Off. . |
| 0 548 599 | 6/1993 | European Pat. Off. . |
| 0 549 271 | 6/1993 | European Pat. Off. . |
| 0 579 659 | 1/1994 | European Pat. Off. . |
| 0 583 536 | 2/1994 | European Pat. Off. . |
| 0 591 282 | 4/1994 | European Pat. Off. . |
| 0 630 964 | 12/1994 | European Pat. Off. . |
| 0 693 550 | 1/1996 | European Pat. Off. . |
| 24 12 837 | 10/1974 | Germany . |
| 34 36 194 | 4/1986 | Germany . |
| 42 21 381 | 2/1994 | Germany . |
| 43 00 772 | 7/1994 | Germany . |
| 43 03 320 | 8/1994 | Germany . |
| 44 16 438 | 11/1995 | Germany . |
| 44 17 734 | 11/1995 | Germany . |
| 44 43 177 | 6/1996 | Germany . |
| 04 238 809 | 8/1992 | Japan . |
| 04 260 610 | 9/1992 | Japan . |
| 06 293 900 | 10/1994 | Japan . |
| WO91/08171 | 6/1991 | WIPO . |
| WO92/11347 | 7/1992 | WIPO . |
| WO93/11215 | 6/1993 | WIPO . |
| WO93/16110 | 8/1993 | WIPO . |
| WO94/02597 | 2/1994 | WIPO . |
| WO94/02618 | 2/1994 | WIPO . |
| WO94/18314 | 8/1994 | WIPO . |
| WO94/23053 | 10/1994 | WIPO . |
| WO95/07350 | 3/1995 | WIPO . |
| WO95/27773 | 10/1995 | WIPO . |
| WO95/34628 | 12/1995 | WIPO . |

OTHER PUBLICATIONS

Derwent WPAT Abstract No. 92–301673/37.
Derwent WPAT Abstract No. 91–126878/18.
Derwent WPAT Abstract No. 91–209559/29.
Derwent WPAT Abstract No. 85–290431/47.
Derwent WPAT Abstract No. 88–355215/50.
Derwent WPAT Abstract No. 92–2118091/27.
Derwent WPAT Abstract No. 94–311135/39.
Derwent WPAT Abstract No. 88–093120/14.
Derwent WPAT Abstract No. 89–033330/05.
Derwent WPAT Abstract No. 89–101263/14.
Derwent WPAT Abstract No. 86–100950/16.
Derwent WPAT Abstract No. 85–172443/29.
Derwent WPAT Abstract No. 91–073523/10.
Derwent WPAT Abstract No. 92–350618/43.
Derwent WPAT Abstract No. 93–009585/02.
Weighardt, Die aktiven Zentren in manganhaltigen Metalloproteinen und anorganische Modellkomplexe, Angew. Chem 101:1179–98 (1989).

TRANSITION-METAL COMPLEXES USED AS ACTIVATORS FOR PEROXY COMPOUNDS

BACKGROUND OF THE INVENTION

This invention relates to the use of certain complexes of transition metals with nitrogen-containing polydentate ligands as activators or catalysts for peroxygen compounds, more particularly for bleaching colored stains in the washing of textiles and cleaning of hard surfaces, for example crockery, and to detergents, cleaners and disinfectants containing such activators or catalysts.

Inorganic peroxygen compounds, more particularly hydrogen peroxide, and solid peroxygen compounds which dissolve in water with elimination of hydrogen peroxide, such as sodium perborate and sodium carbonate perhydrate, have long been used as oxidizing agents for disinfecting and bleaching purposes. In dilute solutions, the oxidizing effect of these substances depends to a large extent on the temperature. For example, with $H_2O_2$ or perborate in alkaline bleaching liquors, sufficiently rapid bleaching of soiled textiles is only achieved at temperatures above about 80° C. At lower temperatures, the oxidizing effect of the inorganic peroxygen compounds can be improved by addition of so-called bleach activators for which numerous proposals, above all from the classes of N- or O-acyl compounds, for example polyacylated alkylenediamines, more particularly tetraacetyl ethylenediamine, acylated glycolurils, more particularly tetraacetyl glycoluril, N-acylated hydantoins, hydrazides, triazoles, hydrotriazines, urazoles, diketopiperazines, sulfuryl amides and cyanurates, also carboxylic anhydrides, more particularly phthalic anhydride, carboxylic acid esters, more particularly sodium nonanoyloxybenzenesulfonate, sodium isononanoyloxybenzenesulfonate and acylated sugar derivatives, such as pentaacetyl glucose, can be found in the literature. By adding these substances, the bleaching effect of aqueous peroxide liquors can be increased to such an extent that substantially the same effects are obtained at temperatures of only 60° C. as are obtained with the peroxide liquor alone at 95° C. In the search for energy-saving washing and bleaching processes, operating temperatures well below 60° C. and, more particularly, below 45° C. down to the temperature of cold water have acquired increasing significance in recent years.

At these low temperatures, there is generally a discernible reduction in the effect of known activator compounds. Accordingly, there has been no shortage of attempts to develop more effective activators for this temperature range although the results achieved thus far have not been convincing. A starting point in this connection is the use of the transition metal salts and complexes proposed, for example, in European patent applications EP 392 592, EP 443 651, EP 458 397, EP 544 490 or EP 549 271 as so-called bleaching catalysts. In their case, the high reactivity of the oxidizing intermediates formed from them and the peroxygen compound is presumably responsible for the risk of discoloration of colored fabrics and, in extreme cases, oxidative fabric damage. European patent application EP 630 964 describes certain manganese complexes which do not have a pronounced effect in boosting the bleaching action of peroxygen compounds and which do not decolor dyed textile fibers although they are capable of bleaching soil or dye detached from fibers in wash liquors. German patent application DE 44 16 438 describes manganese, copper and cobalt complexes which can carry ligands from a number of groups of compounds and which are said to be used as bleaching and oxidation catalysts.

DESCRIPTION OF THE INVENTION

The problem addressed by the present invention was to improve the oxidizing and bleaching effect of inorganic peroxygen compounds at low temperatures below 80° C. and, more particularly, in the range from about 15° C. to 55° C.

It has now been found that transition metal complexes containing certain nitrogen-containing compounds with a tripod structure as ligands have a distinct effect as bleaching catalysts.

The present invention relates to the use of complexes of the transition metals manganese, iron, cobalt, ruthenium, molybdenum, titanium, vanadium and/or copper which contain one or more ligands corresponding to general formula I:

(I)

in which R is a direct bond or an optionally amino-substituted alkylene group containing 1 to 4 carbon atoms, A is a fused or non-fused ring system containing at least one nitrogen atom and B is hydrogen, an OH group or has the same meaning as A,
as activators for peroxygen compounds, particularly inorganic peroxygen compounds, in oxidizing, washing, cleaning or disinfecting solutions. In the alkylene groups R, one or more non-adjacent $CH_2$ units, which are not directly attached to the central N atom, may optionally be replaced by NH units.

Compounds corresponding to general formula I may be converted by formal linking modification of their B units into ligands corresponding to general formula II:

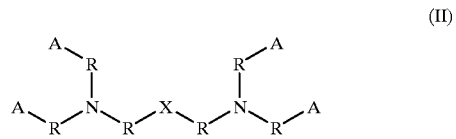

(II)

where A and R are as defined above and X is an optionally hydroxy- and/or $C_{1-4}$-alkyl-substituted phenylene ring or an optionally hydroxysubstituted $C_{1-4}$ alkylene group,
which are each capable of complexing two transition metal atoms. Accordingly, the present invention also relates to the use of optionally binuclear or polynuclear complexes of the transition metals manganese, iron, cobalt, ruthenium, molybdenum, titanium, vanadium and/or copper containing one or more ligands corresponding to general formula II as activators for peroxygen compounds, more particularly inorganic peroxygen compounds, in oxidizing, washing, cleaning or disinfecting solutions.

In the R—B unit of the compounds corresponding to formula I, R is preferably a direct bond where B is hydrogen and is preferably not a direct bond where B is a hydroxyl group. Not all the groups R in one ligand molecule need to be identical. Preferred nitrogen-containing ring systems (A in formulae I and II) include the 2-pyridyl group, the 2-imidazolyl group, the 1-methyl-2-imidazolyl group and the 2-benzimidazolyl group. Not all the groups A in one ligand molecule need be identical. R in the compounds of formula I or II is preferably a methylene group. X in the compounds of formula II is preferably selected from the 1,3-phenylene group, the 2-hydroxy-1,3-phenylene group, the 2-hydroxy-5-methyl-1,3-phenylene group and the hydroxymethylene group.

The compounds of general formulae I or II suitable as ligands for the bleaching catalysts to be used in accordance with the invention may be produced by methods known in principle, as described for example in the review by K. Wieghardt in Angew. Chem. 101 (1989), pages 1179–1198 and the original works cited therein. Normally, commercially available raw materials are converted into the required ligands by condensation reactions, for example with elimination of hydrohalides. The ligands thus obtained may then be reacted with salts of corresponding transition metals, normally in typical solvents. The complexes to be used as bleaching catalysts in accordance with the invention are generally formed at temperatures as low as room temperature and are normally obtained in crystalline form from standard solvents.

The above-mentioned transition metals in the bleaching catalysts to be used in accordance with the invention preferably have oxidation numbers of +2, +3 or +4. Complexes with transition metal central atoms having oxidation numbers of +3 or +4 are preferably used. Systems having mixed oxidation numbers are possible. In the case of polynuclear complexes, not all the metal atoms in the complex need be the same. Preferred complexes include those containing iron and/or manganese as central atoms.

Besides the ligands corresponding to general formulae I and II, the transition metal complexes to be used in accordance with the invention may contain other ligands of generally more simple structure, more particularly neutral or mono- or polyvalent anionic ligands. Suitable other ligands of this type are, for example, water, ammonia, nitrate, nitrite, hydroxide, carbonate, hydrogen carbonate, acetate, formate, citrate, perchlorate and the halides, such as chloride, bromide and iodide, and complex anions, such as hexafluorophosphate. The anionic ligands should provide for charge equalization between the transition metal central atom and the ligand system. If anionic ligands are not present in sufficient numbers to ensure this charge equalization, the cationically charged complexes may contain typical anions, such as sulfate, hydrogen sulfate, methosulfate, ethosulfate, and the anions mentioned above among the anionic ligands as counterions. Oxo ligands, peroxo ligands and imino ligands may also be present. These additional ligands may even have a bridging effect so that polynuclear complexes containing at least one ligand corresponding to general formula I or II are formed.

Preferred bleaching catalysts according to the invention include those containing the tris-(2-pyridylmethyl)-amine ligand:

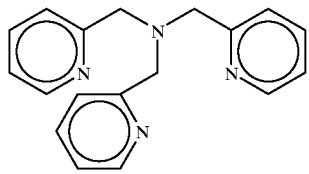

the (bis-((1-methylimidazol-2-yl)-methyl))-(2-pyridylmethyl)-amine ligand:

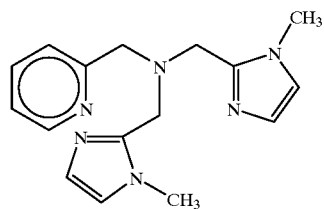

the N-bis-(2-benzimidazolylmethyl)-aminoethanol ligand:

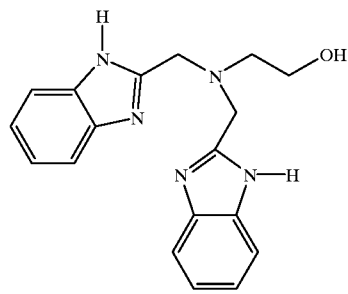

and the N,N'-(bis-(1-methylimidazol-2-yl)-methyl)-ethylenediamine ligand:

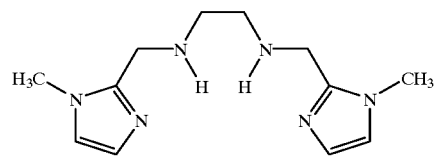

Preferred ligands corresponding to general formula II include 2,6-bis-(bis-(2-benzimidazolylmethyl)-aminomethyl)4-methylphenol:

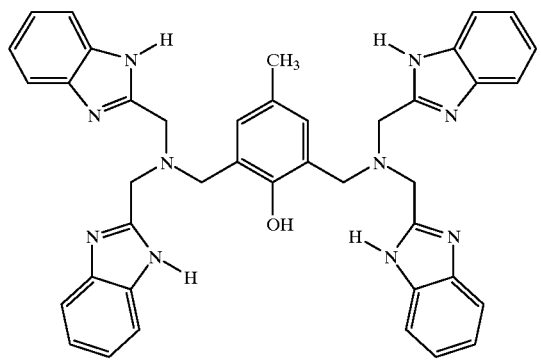

N,N,N',N'-tetrakis-(2-benzimidazolylmethyl)-2-hydroxy-1,3-diaminopropane:

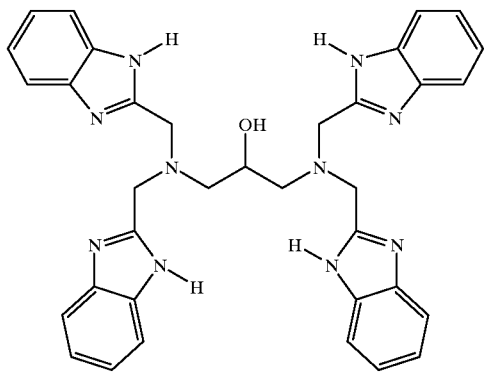

1,3-bis-(bis-(2-benzimidazolylmethyl)-aminomethyl)-benzene:

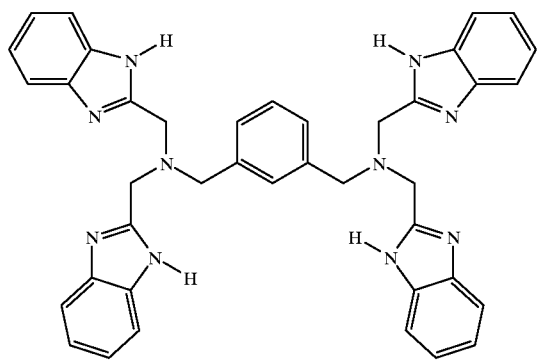

and 2,6-bis-(bis-(2-(pyridylmethyl)-aminomethyl)4-methylphenol:

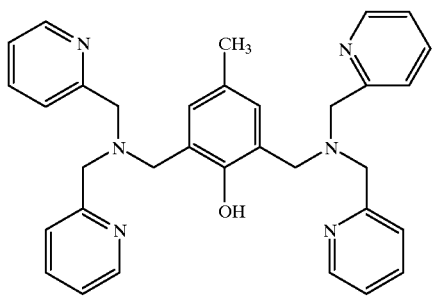

A transition metal bleaching catalyst containing the ligands corresponding to formula I or II is preferably used for bleaching colored stains in the washing of fabrics, particularly in a water-based surfactant-containing liquor. The expression "bleaching of colored stains" is meant to be interpreted in its broadest sense and encompasses both the bleaching of soil present on the fabrics, the bleaching of soil detached from the fabrics and present in the wash liquor and the oxidative destruction of textile dyes present in the wash liquor—which are detached from fabrics under the washing conditions—before they can be absorbed by differently colored fabrics.

In another preferred embodiment, the present invention relates to the use of the transition metal bleaching catalysts containing the ligands corresponding to formula I or II in cleaning solutions for hard surfaces, more particularly for crockery, for bleaching colored stains, more particularly tea stains. In this case, too, the expression "bleaching" encompasses both the bleaching of soil present on the hard surface and the bleaching of soil detached from the hard surface and suspended in the dishwashing liquor.

The present invention also relates to detergents, cleaners and disinfectants containing one of the above-mentioned transition metal bleaching catalysts containing a ligand corresponding to formula I or II and to a process for activating peroxygen compounds using this bleaching catalyst.

In the process according to the invention and in the uses according to the invention, the bleaching catalyst may be used as an activator anywhere where a particular increase in the oxidizing effect of the peroxygen compounds at low temperatures is required, for example in the bleaching of fabrics or hair, in the oxidation of organic or inorganic intermediates and in disinfection.

The use according to the invention essentially comprises creating conditions under which the peroxygen compound and the bleaching catalyst can react with one another with a view to obtaining products with a stronger oxidizing effect. Such conditions prevail in particular when both reactants meet in an aqueous solution. This can be achieved by separately adding the peroxygen compound and the bleaching catalyst to a solution optionally containing a detergent or cleaner. In one particularly advantageous embodiment, however, the process according to the invention is carried out using a detergent, cleaner or disinfectant according to the invention which contains the bleaching catalyst and optionally a peroxidic oxidizing agent. The peroxygen compound may even be separately added to the solution as such or preferably in the form of an aqueous solution or suspension in cases where a peroxygen-free formulation is used.

The conditions can be widely varied according to the application envisaged. Thus, besides purely aqueous solutions, mixtures of water and suitable organic solvents may serve as the reaction medium. The quantities of peroxygen compounds used are generally selected so that the solutions contain between 10 ppm and 10% of available oxygen and preferably between 50 and 5000 ppm of available oxygen. The quantity of bleaching catalyst used is also determined by the particular application envisaged. Depending on the required degree of activation, the activator is used in a quantity of 0.00001 mole to 0.025 mole and preferably in a quantity of 0.0001 mole to 0.002 mole per mole of peroxygen compound, although quantities above and below these limits may be used in special cases.

A detergent, cleaner or disinfectant according to the invention preferably contains 0.0025% by weight to 0.25% by weight and, more preferably, 0.01% by weight to 0.1% by weight of the bleaching catalyst containing the ligands of formula I or II in addition to typical ingredients compatible with the bleaching catalyst. The bleaching catalyst may be adsorbed onto supports and/or encapsulated in shell-forming substances by methods known in principle.

In addition to the bleaching catalyst used in accordance with the invention, the detergents, cleaners and disinfectants according to the invention, which may be present in the form of—in particular—powder-form solids, in the form of post-compacted particles or in the form of homogeneous solutions or suspensions, may in principle contain any known ingredients typically encountered in such formulations. In particular, the detergents and cleaners according to the invention may contain builders, surfactants, organic and/or inorganic peroxygen compounds, water-miscible organic solvents, enzymes, enzyme stabilizers, sequestering agents, electrolytes, pH regulators and other auxiliaries, such as optical brighteners, redeposition inhibitors, dye transfer inhibitors, foam regulators, additional peroxygen activators, dyes and perfumes.

In addition to the ingredients mentioned thus far, a disinfectant according to the invention may contain typical antimicrobial agents to enhance its disinfecting effect on special germs. Antimicrobial additives of the type in question are present in the disinfectants according to the invention in quantities of preferably not more than 10% by weight and, more preferably, in quantities of 0.1% by weight to 5% by weight.

The present invention also relates to a machine dishwashing detergent containing 15% by weight to 65% by weight and, more particularly, 20% by weight to 55% by weight of a water-soluble builder component, 5% by weight to 25% by weight and, more particularly, 8% by weight to 17% by weight (based on the detergent as a whole) of an oxygen-based bleaching agent containing a bleach-catalyzing transition metal complex containing the ligands corresponding to formula I or II, more particularly in quantities of 0.005% by weight to 0.1% by weight. A detergent such as this is, in particular, a low-alkalinity detergent, i.e. a 1% by weight solution has a pH value in the range from 8 to 11.5 and preferably in the range from 9 to 11.

Conventional bleach activators, i.e. compounds which form optionally substituted perbenzoic acid and/or aliphatic peroxocarboxylic acids containing 1 to 10 and more particularly 2 to 4 carbon atoms under perhydrolysis conditions, may be used in addition to the transition metal bleaching catalysts, particularly in combination with inorganic peroxygen compounds. Suitable conventional bleach activators are the typical bleach activators mentioned at the beginning which contain O- and/or N-acyl groups with the number of carbon atoms mentioned and/or optionally substituted benzoyl groups. Preferred conventional bleach activators are polyacylated alkylenediamines, more particularly tetraacetyl ethylenediamine (TAED), acylated glycolurils, more particularly tetraacetyl glycoluril (TAGU), acylated triazine derivatives, more particularly 1,5-diacetyl-2,4-dioxohexahydro-1,3,5-triazine (DADHT), acylated phenol sulfonates, more particularly nonanoyl or isononanoyloxybenzenesulfonate, acylated polyhydric alcohols, more particularly triacetin, ethylene glycol diacetate and 2,5-diacetoxy-2,5-dihydrofuran, and acetylated sorbitol and mannitol, acylated sugar derivatives, more particularly pentaacetyl glucose (PAG), pentaacetyl fructose, tetaacetyl xylose and octaacetyl lactose and acetylated, optionally N-alkylated glucamine and gluconolactone. The combinations of conventional bleach activators known from German patent application DE 44 43 177 may also be used. In one preferred embodiment, the formulations according to the invention contain 1% by weight to 10% by weight and, more particularly, 2% by weight to 6% by weight of such compounds forming peroxocarboxylic acid under perhydrolysis conditions in addition to the bleach-boosting transition metal complex. The ratio by weight of the compound forming peroxocarboxylic acid under perhydrolysis conditions to the transition metal complex compound is preferably in the range from 8000:1 to 1:1 and more preferably in the range from 1000:1 to 10:1. The presence of additional transition metal bleaching catalysts which do not contain a ligand corresponding to formula I or II is also possible.

The formulations according to the invention may contain one or more surfactants, more particularly anionic surfactants, nonionic surfactants and mixtures thereof. Suitable nonionic surfactants are, in particular, alkyl glycosides and ethoxylation and/or propoxylation products of alkyl glycosides or linear or branched alcohols containing 12 to 18 carbon atoms in the alkyl group and 3 to 20 and preferably 4 to 10 alkyl ether groups. Corresponding ethoxylation and/or propoxylation products of N-alkylamines, vicinal diols, fatty acid esters and fatty acid amides corresponding to the long-chain alcohol derivatives in regard to the alkyl moiety and of alkylphenols containing 5 to 12 carbon atoms in the alkyl group may also be used.

Suitable anionic surfactants are, in particular, soaps and those which contain sulfate or sulfonate groups preferably having alkali metal ions as cations. Preferred soaps are the alkali metal salts of saturated or unsaturated fatty acids containing 12 to 18 carbon atoms. Fatty acids such as these need not even be completely neutralized for use in accordance with the invention. Suitable surfactants of the sulfate type include salts of sulfuric acid semi-esters of fatty alcohols containing 12 to 18 carbon atoms and sulfation products of the nonionic surfactants mentioned with a low degree of ethoxylation. Suitable surfactants of the sulfonate type include linear alkylbenzenesulfonates containing 9 to 14 carbon atoms in the alkyl moiety, alkanesulfonates containing 12 to 18 carbon atoms which are formed in the reaction of corresponding monoolefins with sulfur trioxide and also $\alpha$-sulfofatty acid esters which are formed in the sulfonation of fatty acid methyl or ethyl esters.

Surfactants such as these are present in the cleaners or detergents according to the invention in quantities of, preferably, 5% by weight to 50% by weight and, more preferably, 8% by weight to 30% by weight while the disinfectants according to the invention and machine dishwashing detergents according to the invention preferably contain 0.1% by weight to 20% by weight and, more preferably, 0.2% by weight to 10% by weight of surfactants.

Particularly suitable peroxygen compounds are organic peracids or peracidic salts of organic acids, such as phthalimidopercaproic acid, perbenzoic acid or salts of diperdodecane diacid, hydrogen peroxide and inorganic salts which give off hydrogen peroxide under the reaction conditions, such as perborate, percarbonate and/or persilicate. If solid per compounds are to be used, they may be employed in the form of powders or granules which may even be coated in known manner. The peroxygen compounds may be added to the wash or cleaning liquor either as such or in the form of formulations containing them which, in principle, may comprise all the usual ingredients of detergents, cleaners or disinfectants. In one particularly preferred embodiment, alkali metal percarbonate, alkali metal perborate monohydrate or hydrogen peroxide is used in the form of an aqueous solution containing 3% by weight to 10% by weight of hydrogen peroxide. If a detergent or cleaner according to the invention contains peroxygen compounds, the peroxygen compounds are present in quantities of preferably up to 50% by weight and, more preferably, in quantities of 5% by weight to 30% by weight whereas the disinfectants according to the invention preferably contain from 0.5% by weight to 40% by weight and, more preferably, from 5% by weight to 20% by weight of peroxygen compounds.

A formulation according to the invention preferably contains at least one water-soluble and/or water-insoluble, organic and/or inorganic builder. Water-soluble organic builders include polycarboxylic acids, more particularly citric acid and sugar acids, monomeric and polymeric aminopolycarboxylic acids, more particularly methyl glycine diacetic acid, nitrilotriacetic acid and ethylenediamine tetraacetic acid, and polyaspartic acid, polyphosphonic acids, more particularly aminotris-(methylenephosphonic acid), ethylenediamine tetrakis(methylenephosphonic acid) and 1-hydroxyethane-1,1-diphosphonic acid, polymeric hydroxy compounds, such as dextrin, and polymeric (poly)carboxylic acids, more particularly the polycarboxylates obtainable by oxidation of polysaccharides according to International patent application WO 93/16110, polymeric acrylic acids, methacrylic acids, maleic acids and copolymers thereof which may also contain small amounts of polymerizable substances with no carboxylic acid functionality in copolymerized form. The relative molecular weight of the homopolymers of unsaturated carboxylic acids is generally in the range from 5,000 to 200,000 while the relative molecular weight of the copolymers is between 2,000 and 200,000 and preferably between 50,000 and 120,000, based on free acid. A particularly preferred acrylic acid/maleic acid copolymer has a relative molecular weight of 50,000 to 100,000. Suitable, albeit less preferred, compounds of this class are copolymers of acrylic acid or methacrylic acid with vinyl ethers, such as vinyl methyl ethers, vinyl esters, ethylene, propylene and styrene, in which the acid makes up at least 50% by weight of the copolymer. Other suitable water-soluble organic builders are terpolymers which contain two unsaturated acids and/or salts thereof as monomers and vinyl alcohol and/or a vinyl alcohol derivative or a carbohydrate as the third monomer. The first acidic monomer or its salt is derived from a monoethylenically unsaturated $C_{3-8}$ carboxylic acid and preferably from a $C_{3-4}$ monocarboxylic acid, more particularly from (meth)acrylic acid. The second acidic monomer or its salts may be a derivative of a $C_{4-8}$ dicarboxylic acid, maleic acid being particularly preferred. In this case, the third monomeric unit is formed by vinyl alcohol and/or preferably an esterified vinyl alcohol. Vinyl alcohol derivatives representing an ester of short-chain carboxylic acids, for example $C_{1-4}$ carboxylic acids, with vinyl alcohol are particularly preferred. Preferred polymers contain 60% by weight to 95% by weight and, more particularly, 70% by weight to 90% by weight of (meth)acrylic acid or (meth)acrylate, preferably acrylic acid or acrylate and maleic acid or maleate, and 5% by weight to 40% by weight and preferably 10% by weight to 30% by weight of vinyl alcohol and/or vinyl acetate. Polymers in which the ratio by weight of (meth)acrylic acid or (meth) acrylate to maleic acid or maleate is between 1:1 and 4:1, preferably between 2:1 and 3:1 and more preferably between 2:1 and 2.5:1 are most particularly preferred. Both the quantities and the ratios by weight mentioned are based on the acids. The second acidic monomer or its salt may even be a derivative of an allyl sulfonic acid substituted in the 2-position by an alkyl group, preferably a $C_{1-4}$ alkyl group, or by an aromatic group preferably derived from benzene or benzene derivatives. Preferred terpolymers contain 40% by weight to 60% by weight and, more particularly, 45% by weight to 55% by weight of (meth)acrylic acid or (meth) acrylate, preferably acrylic acid or acrylate, 10% by weight to 30% by weight and preferably 15% by weight to 25% by weight of methallyl sulfonic acid or methallyl sulfonate and, as the third monomer, 15% by weight to 40% by weight and preferably 20% by weight to 40% by weight of a carbohydrate. This carbohydrate may be, for example, a mono-, di-, oligo- or polysaccharide, mono-, di- or oligosaccharides being preferred. Sucrose is particularly preferred. The use of the third monomer presumably introduces predetermined weak spots into the polymer which are responsible for its ready biodegradability. These terpolymers may be produced in particular by the processes described in German patent DE 42 21 381 and in German patent application DE 43 00 772 and generally have a relative molecular weight in the range from 1,000 to 200,000, preferably in the range from 200 to 50,000 and more preferably in the range from 3,000 to 10,000. Other preferred copolymers are the copolymers which are described in German patent applications DE 43 03 320 and DE 4417 734 and which preferably contain acrolein and acrylic acid/acrylic acid salts or vinyl acetate as monomers. The organic builders may be used in the form of aqueous solutions, preferably 30 to 50% by weight aqueous solutions, particularly for the production of liquid formulations. All the acids mentioned are generally used in the form of their water-soluble salts, more particularly their alkali metal salts.

If desired, organic builders of the type in question may be present in quantities of up to 50% by weight, more particularly in quantities of up to 25% by weight and preferably in quantities of 1% by weight to 8% by weight. Quantities near the upper limit mentioned are preferably used in paste-form or liquid, more particularly water-containing, formulations according to the invention.

Particularly suitable water-soluble inorganic builders are alkali metal phosphates which may be present in the form of their alkaline, neutral or acidic sodium or potassium salts. Examples include trisodium phosphate, tetrasodium diphosphate, disodium dihydrogen diphosphate, pentasodium triphosphate, so-called sodium hexametaphosphate, oligomeric trisodium phosphate with degrees of oligomerization of 5 to 1000 and, more particularly, 5 to 50 and the corresponding potassium salts or mixtures of sodium or potassium salts. Alkali metal alumosilicates, more particularly crystalline or amorphous alkali metal alumosilicates, are used as water-insoluble, water-dispersible inorganic builders in quantities of up to 50% by weight and preferably in quantities of not more than 40% by weight and, in liquid formulations, particularly in quantities of 1% by weight to 5% by weight. Of these inorganic builders, detergent-range crystalline sodium alumosilicates, more particularly zeolite A, P and optionally X, are preferred. Quantities approaching the upper limit mentioned are preferably used in solid particulate formulations. Suitable alumosilicates contain in particular no particles larger than 30 $\mu$m in size, at least 80% by weight preferably consisting of particles below 10 $\mu$m in size. Their calcium binding capacity, which may be determined in accordance with German patent DE 24 12 837, is generally in the range from 100 to 200 mg CaO per gram.

Suitable substitutes or partial substitutes for the alumosilicate mentioned are crystalline alkali metal silicates which may be present either on their own or in the form of a mixture with amorphous silicates. The alkali metal silicates suitable for use as builders in the formulations according to the invention preferably have a molar ratio of alkali metal oxide to $SiO_2$ of less than 0.95:1 and, more particularly, from 1:1.1 to 1:12 and may be present in amorphous or crystalline form. Preferred alkali metal silicates are the sodium silicates, more particularly the amorphous sodium silicates, with a molar $Na_2O:SiO_2$ ratio of 1:2 to 1:2.8. Those with a molar $Na_2O:SiO_2$ ratio of 1:1.9 to 1:2.8 may be produced by the process according to European patent application EP 0 425 427. Preferred crystalline silicates, which may be present either on their own or in the form of a mixture with amorphous silicates, are crystalline layer silicates with the general formula $Na_2Si_xO_{2x+1}+\cdot yH_2O$, where x—the so-called modulus—is a number of 1.9 to 4 and y is a number of 0 to 20, preferred values for x being 2, 3 or 4. Crystalline layer silicates which correspond to this general formula are described, for example, in European patent application EP 0 164 514. Preferred crystalline layer silicates are those in which x in the general formula mentioned assumes a value of 2 or 3. Both β- and σ-sodium disilicates ($Na_2Si_2O_5 \cdot yH_2O$) are particularly preferred, -disodium disilicate being obtainable, for example, by the process described in International patent application WO 91/08171. σ-Sodium silicates with a modulus of 1.9 to 3.2 may be produced in accordance with Japanese patent applications JP 04/238 809 or JP 04/260 610. Substantially water-free crystalline alkali metal silicates corresponding to the above general formula, in which x is a number of 1.9 to 2.1, obtainable from amorphous alkali metal silicates as described in European patent applications EP 0 548 599, EP 0 502 325 and EP 0 425 428, may also be used in the formulations according to the invention. Another preferred embodiment of formulations according to the invention uses a crystalline sodium layer silicate with a modulus of 2 to 3 obtainable from sand and soda by the process according to European patent application EP 0 436 835. Crystalline sodium silicates with a modulus of 1.9 to 3.5 obtainable by the processes according to European patents EP 0 164 552 and/or EP 0 294 753 are used in another preferred embodiment of the formulations according to the invention. If alkali metal alumosilicate, particularly zeolite, is present as an additional builder, the ratio by weight of alumosilicate to silicate, expressed as water-free active substances, is preferably from 1:10 to 10:1. In formulations containing both amorphous and crystalline alkali metal silicates, the ratio by weight of amorphous alkali metal silicate to crystalline alkali metal silicate is preferably 1:2 to 2:1 and, more preferably, 1:1 to 2:1.

Builders are present in the detergents or cleaners according to the invention in quantities of, preferably, up to 60% by weight and, more preferably, from 5% by weight to 40% by weight while the disinfectants according to the invention are preferably free from the builders which only complex the components of water hardness and contain preferably no more than 20% by weight and, more preferably, from 0.1% by weight to 5% by weight of heavy metal complexing agents, preferably from the group consisting of aminopolycarboxylic acids, aminopolyphosphonic acids and hydroxypolyphosphonic acids and water-soluble salts and mixtures thereof.

In one preferred embodiment, machine dishwashing detergents according to the invention contain typical alkali carriers such as, for example, alkali metal silicates, alkali metal carbonates and/or alkali metal hydrogen carbonates. The alkali carriers normally used include carbonates, hydrogen carbonates and alkali metal silicates with a molar $SiO_2:M_2O$ (M=alkali metal atom) ratio of 1:1 to 2.5:1. Alkali metal silicates may be present in quantities of up to 40% by weight, based on the detergent as a whole. However, the highly alkaline metasilicates are preferably not used at all as alkali carriers. The alkali carrier system preferably used in detergents according to the invention such as these is a mixture of carbonate and hydrogen carbonate, preferably sodium carbonate and hydrogen carbonate, which is present in a quantity of up to 50% by weight and, preferably, in a quantity of 5% by weight to 40% by weight. The ratio of carbonate used to hydrogen carbonate used varies according to the pH value ultimately required.

In another preferred embodiment, dishwashing detergents according to the invention contain 20% by weight to 60% by weight of water-soluble organic builder, more particularly alkali metal citrate, 3% by weight to 20% by weight of alkali metal carbonate and 5% by weight to 40% by weight of alkali metal disilicate.

Enzymes suitable for use in the detergents/cleaners/disinfectants are enzymes from the class of proteases, lipases, cutinases, amylases, pullulanases, hemicellulases, cellulases, oxidases and peroxidases and mixtures thereof. Particularly suitable enzymes are those obtained from fungi or bacteria, such as *Bacillus subtilis, Bacillus licheniformis, Streptomyces griseus, Humicola lanuginosa, Humicola insolens, Pseudomonas pseudoalcaligenes* or *Pseudomonas cepacia*, for example proteases, such as BLAP®, Optimase®, Opticlean®, Maxacal®, Maxapem®, Esperase® and/or Savinase®; amylases, such a Termamyl®, Amylase-LT®, Maxamyl®, Duramyl® and/or Purafect® OxAm; lipases, such as Lipolase®, Lipomax®, Lumafast® and/or Lipozym®. As described for example in International patent applications WO 92/11347 or WO 94123005, the enzymes optionally used may be adsorbed onto supports and/or encapsulated in shell-forming substances to protect them against premature inactivation. They are added to the detergents, cleaners and disinfectants according to the invention in quantities of preferably not more than 5% by weight and, more preferably between 0.2% by weight and 3% by weight, enzymes stabilized against oxidative degradation, as known for example from International patent applications WO 94/02597, WO 94/02618, WO 94/18314, WO 94/23053 or WO 95/07350, being particularly preferred.

Typical enzyme stabilizers optionally present, particularly in liquid formulations according to the invention, include aminoalcohols, for example mono-, di-, tri-ethanolamine and propanolamine and mixtures thereof, the lower carboxylic acids known, for example, from European patent applications EP 376 705 and EP 378 261, boric acid and alkali metal borates, the boric acid/carboxylic acid combinations known, for example, from European patent application EP 451 921, the boric acid esters known, for example, from International patent application WO 93/11215 or from European patent application EP 511 456, the boron acid derivatives known, for example, from European patent application EP 583 536, calcium salts, for example the calcium/formic acid combination known from European patent EP 28 865, the magnesium salts known, for example, from European patent application EP 378 262 and/or the sulfur-containing reducing agents known, for example, from European patent applications EP 080 748 and EP 080 223.

Suitable foam inhibitors include long-chain soaps, more particularly behenic soap, fatty acid amides, paraffins, waxes, microcrystalline waxes, organopolysiloxanes and mixtures thereof which may additionally contain microfine, optionally silanized or otherwise hydrophobicized silica. For use in particulate formulations, these foam inhibitors are preferably fixed to granular water-soluble supports as described, for example, in DE-OS 34 36 194, in European patent applications EP 262 588, EP 301 414 and EP 309 931 or in European patent EP 150 386.

In addition, a detergent according to the invention may contain redeposition inhibitors. The function of redeposition inhibitors is to keep the soil suspended from the fibers suspended in the liquor and thus to prevent discoloration of the fibers. Suitable redeposition inhibitors are water-soluble, generally organic colloids, for example the water-soluble salts of polymeric carboxylic acids, glue, gelatine, salts of ether carboxylic acids or ether sulfonic acids of starch or cellulose or salts of acidic sulfuric acid esters of cellulose or starch. Water-soluble polyamides containing acidic groups are also suitable for this purpose. Soluble starch preparations and other starch products than those mentioned above, for example partially hydrolyzed starch, may also be used. Sodium carboxymethyl cellulose, methyl cellulose, methylhydroxyethyl cellulose and mixtures thereof are preferably used.

Organic solvents suitable for use in the formulations according to the invention, particularly where they are present in liquid or paste-like form, include alcohols containing 1 to 4 carbon atoms, more particularly methanol, ethanol, isopropanol and tert.butanol, diols containing 2 to 4 carbon atoms, more particularly ethylene glycol and propylene glycol, and mixtures thereof and the ethers derived from compounds belonging to the classes mentioned above. Water-miscible solvents such as these are present in the detergents, cleaners and disinfectants according to the invention in quantities of preferably not more than 30% by weight and, more preferably, in quantities of 6% by weight to 20% by weight.

To establish a desired pH value which is not automatically adjusted by the mixture of the other components, the formulations according to the invention may contain system-compatible and ecologically compatible acids, more particularly citric acid, acetic acid, tartaric acid, malic acid, lactic acid, glycolic acid, succinic acid, glutaric acid and/or adipic acid, and mineral acids, more particularly sulfuric acid, or bases, more particularly ammonium or alkali metal hydroxides. pH regulators such as these are present in the formulations according to the invention in quantities of preferably not more than 20% by weight and, more preferably, between 1.2% by weight and 17% by weight.

Although it is known that transition metal complexes can counteract the corrosion of silver, the bleach-catalyzing complexes according to the invention are generally used in quantities which are too small to be able to protect silver against corrosion so that silver corrosion inhibitors may be additionally used in dishwashing detergents according to the invention.

Preferred silver corrosion inhibitors are organic sulfides, such as cystine and cysteine, dihydric or trihydric phenols, optionally alkyl-, aminoalkyl- or aryl-substituted triazoles, such as benzotriazole, isocyanuric acid, manganese, iron, cobalt, ruthenium, molybdenum, titanium, vanadium and/or copper salts and/or complexes in which the metals mentioned may have one of the oxidation numbers II, III, IV, V or VI, depending on the metal.

The production of the solid formulations according to the invention does not involve any difficulties and may be carried out by methods known in principle, for example by spray drying or granulation, the peroxygen compound and bleaching catalyst optionally being added later. To produce formulations according to the invention with high bulk density, more particularly in the range from 650 g/l to 950 g/l, a process comprising an extrusion step known from European patent EP 486 592 is preferably applied. Detergents, cleaners or disinfectants according to the invention in the form of aqueous solutions or solutions containing other typical solvents are produced with particular advantage simply by mixing the ingredients which may be introduced into an automatic mixer either as such or in the form of a solution. In one preferred embodiment of machine dishwashing formulations, the formulations are produced in the form of tablets by the processes disclosed in European patents EP 0 579 659 and EP 0 591 282.

EXAMPLES

Example 1

Production of an Mn bleaching catalyst to be used in accordance with the invention 1.A: Synthesis of tris-(2-pyridylmethyl)-amine (tpa)

5.0 g (30.5 mmoles) of 2-picolyl chloride hydrochloride were dissolved in 13 ml of water and 6 ml of 5.3 N NaOH were added to the resulting solution while cooling with ice. The red suspension obtained was cooled to 0° C. and a solution of 1.64 g (15.25 mmoles) of picolylamine in 26 ml of dichloromethane was added. The mixture was heated to room temperature and reacted with another 6 ml of 5.3 N NaOH over a period of several days during which measures were taken to ensure that the pH value did not rise above 9.5. The mixture was then washed twice with 7 ml of 15% NaOH and the organic phase was dried over sodium sulfate. After the drying agent had been removed, the solvent was evaporated off. The brown residue was extracted with ether and the solid obtained was recrystallized from ether. 2.4 g of tris-(2-pyridylmethyl)-amine were obtained.

1.B: Synthesis of $[Mn_2(tpa)_2(OAc)_2](OAc)_2$ (B1)

2.45 g (10 mmoles) of $Mn(OAc)_2 \cdot 4H_2O$ and 2.7 g (20 mmoles) of sodium acetate were dissolved in methanol and reacted with 2.9 g (10 mmoles) of tpa. The solution was stirred for 2 h at room temperature and then cooled for 24 h to 0° C. The dark brown solid formed was separated off and dried (2.2 g).

Example 2

Production of an Fe bleaching catalyst to be used in accordance with the invention 2.A: Synthesis of N,N,N',N'-tetrakis(2-(1-methylbenzimidazolyl))-2-hydroxy-1,3-diaminopropane (tbpo)

1.06 g (9.7 mmoles) of 1,2-diaminobenzene were thoroughly mixed with 0.5 g (1.6 mmoles) of 2-hydroxy-1,3-diaminopropane tetraacetic acid and heated to 170–180° C. The mixture was cooled and taken up with about 15 ml of 4 N HCl. A grey deposit was formed, filtered off and washed with acetate. The solid was dissolved in water and neutralized with dilute ammonia. The white deposit was removed, recrystallized from acetone and dried. 0.5 g of the diaminopropane derivative was obtained.

2.B: Synthesis of $[Fe_2(tbpo)(OAc)_2](ClO_4)_3$ (B2)

2.58 g (5 mmoles) of $Fe(ClO_4)_3 \cdot 9H_2O$ and 2.7 g (20 mmoles) of sodium acetate were dissolved in about 50 ml of methanol and 1.53 g (2.5 mmoles) of tbpo were added to the resulting solution. The solution was stirred for 2 h at room temperature and then cooled for 24 h to 0° C. The green-brown solid formed was separated off and dried (1.6 g).

Example 3

98 mg of sodium perborate monohydrate were dissolved in a solution containing 2.5 mg of morine in 99.5 ml of deionized water. The pH was adjusted to 9.5 and was kept at that value throughout the following measuring time by means of a pH stat. The temperature was also kept constant at 20° C. 0.5 ml of a solution containing the bleaching catalyst to be tested in a concentration of 50 ppm, based on transition metal, was added. The extinction E of the solution at 400 nm was measured at 1 minute intervals over a period of 30 minutes. The values for the percentage decoloration D(t), calculated in accordance with $D(t)=[E(t)-E(O)]/E(O) \cdot 100$ are set out in the following Table.

The manganese complex (B1) containing the tris-(2-pyridylmethyl)-amine ligand produced in accordance with Example 1 and the iron complex (B2) containing the N,N,N',N'-tetrakis-(2-(1-methylbenzimidazolyl))-2-hydroxy-1,3-diaminopropane ligand produced in accordance with Example 2 were tested in accordance with the invention. For comparison, the conventional bleach activator N,N,N',N'-tetraacetyl ethylenediamine (TAED) was also tested otherwise the same conditions, but in a concentration of 6% by weight (C1)

TABLE 1

Percentage decoloration as a function of time

| Beach activator or catalyst | Decoloration after | | |
|---|---|---|---|
| | 5 mins. | 15 mins. | 28 mins. |
| B1 | 84 | 94 | 95 |
| B2 | 34 | 56 | 81 |
| C | 35 | 63 | 84 |

It can be seen that a significantly better bleaching effect can be achieved by the use according to the invention (B1 and B2) than by the conventional bleach activator TAED in a far higher concentration (C1).

What is claimed is:

1. A method of activating a peroxygen compound in an oxidizing, washing, cleaning or disinfecting solution, comprising the step of contacting said peroxygen compound with one or more complexes of one or more metals selected from the group consisting of manganese, iron, cobalt, ruthenium, molybdenum, titanium, vanadium, and copper containing a ligand of the formula I

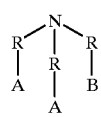
(I)

or formula II

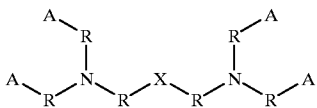
(II)

wherein each R independently is a bond, a $C_1$ to $C_4$ alkylene group, a $C_1$ to $C_4$ amino substituted alkylene group or a $C_1$ to $C_4$ alkylene group wherein one or more non-adjacent $CH_2$ units, which are not directly attached to the central N atom, are replaced by NH units, each A is the same or different and is 2-imidazolyl, 1-methyl-2-imidazolyl, or 2-benzimidazolyl, B is A or OH, and X is an optionally hydroxy- and/or $C_1$ to $C_4$ alkyl-substituted phenylene ring or an optionally hydroxysubstituted $C_1$ to $C_4$ alkylene group.

2. A method according to claim 1, wherein the metal is iron, manganese, or both iron and manganese.

3. A method according to claim 1, wherein the metal has an oxidation number of +2, +3, or +4.

4. A method according to claim 1, wherein R is not a bond when B is OH.

5. A method according to claim 1, wherein R is methylene.

6. A method according to claim 1, wherein X is selected from the group consisting of 1,3-phenylenyl, 2-hydroxy-1, 3-phenylenyl, 2-hydroxy-5-methyl-1,3-phenylenyl, and hydroxymethylenyl.

7. A method of activating a peroxygen compound in an oxidizing, washing, cleaning or disinfecting solution, comprising the step of contacting said peroxygen compound with one or more complexes of one or more metals selected from the group consisting of manganese, cobalt, molybdenum, titanium, vanadium, and copper containing a ligand of the formula I

(I)

or formula II

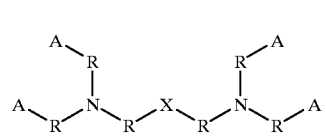
(II)

wherein each R independently is a bond, a $C_1$ to $C_4$ alkylene group, a $C_1$ to $C_4$ amino-substituted alkylene group or a $C_1$ to $C_4$ alkylene group wherein one or more non-adjacent $CH_2$ units which are not directly attached to the central N atom, are replaced by NH units, each A is the same or different and is 2-pyridyl, 2-imidazolyl, 1-methyl-2-imidazolyl, or 2-benzimidazolyl, B is A or OH, and X is an optionally hydroxy- and/or $C_1$ to $C_4$ alkyl-substituted phenylene ring or an optionally hydroxysubstituted $C_1$ to $C_4$ alkylene group.

8. A method according to claim 7, wherein the metal is manganese.

9. A method according to claim 7, wherein the metal has an oxidation number of +2, +3, or +4.

10. A method according to claim 7, wherein R is not a bond when B is OH.

11. A method according to claim 7, wherein R is methylene.

12. A method according to claim 7, wherein X is selected from the group consisting of 1,3-phenylenyl, 2-hydroxy-1, 3-phenylenyl, 2-hydroxy-5-methyl-1,3-phenylenyl, and hydroxymethylenyl.

13. The method of claim 1 or claim 7, comprising the steps of forming a solution comprising water or water and one or more water-miscible organic solvents selected from the group consisting of alcohols of 1–4 carbons, diols of 2 to 4 carbons and ethers derived from said alcohols or diols with an amount of the peroxygen compound sufficient to provide the solution with 50 to 5000 ppm of available oxygen, and contacting the peroxygen compound with 0.0001 to 0.025 moles of one or more of the complexes of formula I or formula II per mole of peroxygen compound.

* * * * *